(12) United States Patent
Pasch (10) Patent No.: US 11,125,656 B2
(45) Date of Patent: Sep. 21, 2021

(54) ENCASED SOIL AUGER APPARATUS FOR ARCHEOLOGICAL ASSESSMENTS AND METHOD OF OPERATING THE SAME

(71) Applicant: Chelsea Pasch, New Brunswick (CA)

(72) Inventor: Chelsea Pasch, New Brunswick (CA)

( * ) Notice: Subject to any disclaimer, the term of this patent is extended or adjusted under 35 U.S.C. 154(b) by 255 days.

(21) Appl. No.: 16/345,417

(22) PCT Filed: Feb. 3, 2017

(86) PCT No.: PCT/CA2017/000024
§ 371 (c)(1),
(2) Date: Apr. 26, 2019

(87) PCT Pub. No.: WO2018/076095
PCT Pub. Date: May 3, 2018

(65) Prior Publication Data
US 2019/0250072 A1 Aug. 15, 2019

(30) Foreign Application Priority Data
Oct. 28, 2016 (CA) .................................. CA 2946944

(51) Int. Cl.
*G01N 1/08* (2006.01)
*E21B 10/44* (2006.01)
*E21B 49/02* (2006.01)
*E02D 1/04* (2006.01)
*E21B 7/00* (2006.01)
*G01N 33/24* (2006.01)

(52) U.S. Cl.
CPC .................. *G01N 1/08* (2013.01); *E02D 1/04* (2013.01); *E21B 7/005* (2013.01); *E21B 10/44* (2013.01); *E21B 49/02* (2013.01); *G01N 33/24* (2013.01)

(58) Field of Classification Search
CPC .......... E21B 49/02; E21B 7/005; E21B 10/44; E21B 7/201; G01N 1/08; G01N 33/24; E02D 1/04
See application file for complete search history.

(56) References Cited

U.S. PATENT DOCUMENTS

| | | | | |
|---|---|---|---|---|
| 2,735,703 A | * | 2/1956 | Goodman | E21B 10/44 |
| | | | | 403/61 |
| 3,565,190 A | * | 2/1971 | Ishii | E21B 17/22 |
| | | | | 175/171 |
| 4,228,862 A | * | 10/1980 | Causse | E21B 7/002 |
| | | | | 175/242 |
| 4,653,336 A | | 3/1987 | Vollweiler | |

(Continued)

OTHER PUBLICATIONS

PCT, Canadian Intellectual Property Office (ISA/CA), International Search Report, International Application No. PCT/CA2017/000024, 3 pages (dated Jul. 25, 2017).

(Continued)

*Primary Examiner* — Benjamin R Schmitt
(74) *Attorney, Agent, or Firm* — Thompson Hine LLP (57) ABSTRACT

An encased soil auger apparatus is provided. The encased soil auger apparatus comprises an auger casing forming a hollow cylindrical body. A wall of the auger casing has a plurality of openings having a predetermined size for enabling passage of particles therethrough. A soil auger having a helical screw blade is disposed in the auger casing in a coaxial fashion. A soil engaging end portion of the auger protrudes a first end of the auger casing.

11 Claims, 8 Drawing Sheets

(56) References Cited

U.S. PATENT DOCUMENTS

| | | | |
|---|---|---|---|
| 5,245,878 A | 9/1993 | Underwood | |
| 5,476,017 A * | 12/1995 | Pinto | G01N 1/08 |
| | | | 73/864.62 |
| 7,546,887 B2 | 6/2009 | Schwab | |
| 8,365,638 B2 | 2/2013 | Paxton | |

OTHER PUBLICATIONS

PCT, Canadian Intellectual Property Office (ISA/CA), Written Opinion of the International Searching Authority, International Application No. PCT/CA2017/000024, 3 pages (dated Jul. 25, 2017).

* cited by examiner

ENCASED SOIL AUGER APPARATUS FOR ARCHEOLOGICAL ASSESSMENTS AND METHOD OF OPERATING THE SAME

CROSS-REFERENCE TO RELATED APPLICATIONS

This application is a national stage filing of International Application No. PCT/CA2017/000024, International Publication No. WO 2018/076095, filed on Feb. 3, 2017, which claims priority to Canadian Patent Application No. 2,946,944, filed on Oct. 28, 2016. The entire contents of both of these applications are incorporated by reference herein.

FIELD

The present invention relates to systematic archaeological test pitting, and more particularly, to an encased soil auger apparatus for mechanical extraction and processing of soil for archeological assessments and a method of operating the same.

BACKGROUND

Present-day archaeological testing of areas of archaeological potential is conducted by manually excavating numerous test pits—typically, several hundred test pits are excavated for larger scale projects—arranged in a geo-referenced grid covering the area. The standard size of the test pits used by archaeologists to test the ground for archaeological remains is 50 cm by 50 cm cross-section and depth of 120 cm. The soil extracted from the test pits is then, typically manually, screened for archaeological remains before the test pits are back filled.

Manual testing for archaeological remains is extremely labour intensive, costly, and time consuming, typically at a rate of approximately 10 test pits per person per standard 8 hour work day.

Furthermore, manually dug test pits are not of the same size, substantially reducing the accuracy of the testing due to the non-uniformity of the test pits. Another problem of manual testing is "spill-in" of sediments surrounding the test pits—in particular, gravel rich soil—causing cross-contamination of the extracted soil, further reducing the accuracy of the testing.

Manually dug test pits are excavated to a maximum depth of 120 cm to minimize risk of operator injury, thus the testing of particularly older sites is substantially limited, i.e. the manual digging is stopped prior reaching the depths where archaeological remains may be found.

Employment of conventional augers in archaeological testing is limited to very small soil augers. Holes having a diameter substantially smaller than 50 cm are drilled in close proximity to each other and the soil retrieved by the auger is then processed by hand on the surface. Again, the "spill-in" effect is encountered by which soil from the auger and/or profile of the fresh test pit during excavation cross-contaminates the extracted soil.

While employment of tubular soil augers, as disclosed, for example, in U.S. Pat. Nos. 4,653,336 and 8,365,638, increases the sample retaining capacity of the auger, the size of the auger is still substantially limited, as well as the "spill-in" effect is still encountered.

It may be desirable to provide an encased soil auger apparatus for mechanical extraction and processing of soil for archeological assessments that substantially prevents "spill-in" effects.

It also may be desirable to provide an encased soil auger apparatus for mechanical extraction and processing of soil for archeological assessments that enables soil extraction and soil screening using the same apparatus.

It also may be desirable to provide an encased soil auger apparatus for mechanical extraction and processing of soil for archeological assessments that enables provision of water during the soil screening.

It also may be desirable to provide a method of operating an encased soil auger apparatus for mechanical extraction and processing of soil for archeological assessments that enables soil extraction and soil screening using the same apparatus.

SUMMARY

Accordingly, the current disclosure may provide an encased soil auger apparatus for mechanical extraction and processing of soil for archeological assessments that substantially prevents "spill-in" effects.

The disclosure may provide an encased soil auger apparatus for mechanical extraction and processing of soil for archeological assessments that enables soil extraction and soil screening using the same apparatus.

The disclosure may provide an encased soil auger apparatus for mechanical extraction and processing of soil for archeological assessments that enables provision of water during the soil screening.

The disclosure may provide a method of operating an encased soil auger apparatus for mechanical extraction and processing of soil for archeological assessments that enables soil extraction and soil screening using the same apparatus.

According to one aspect, there is provided an encased soil auger apparatus. The encased soil auger apparatus comprises an auger casing forming a hollow cylindrical body. A wall of the auger casing has a plurality of openings having a predetermined size for enabling passage of particles therethrough. A soil auger having a helical screw blade is disposed in the auger casing in a coaxial fashion. A soil engaging end portion of the auger protrudes a first end of the auger casing.

According to another aspect, there is provided an encased soil auger apparatus. The encased soil auger apparatus comprises an auger casing forming a hollow cylindrical body. A wall of the auger casing has a plurality of openings having a predetermined size for enabling passage of particles therethrough. A soil auger having a helical screw blade is disposed in the auger casing in a coaxial fashion. A soil engaging end portion of the auger protrudes a first end of the auger casing. The soil engaging end portion of the auger extends from a longitudinal axis approximately a same distance as an outside radius of the auger casing. The encased soil auger apparatus further comprises an end cap for enclosing the soil engaging end portion of the auger after extraction of the soil.

According to another aspect, there is provided a method of extracting and screening soil. An encased soil auger apparatus is provided. The encased soil auger apparatus is placed at a predetermined location with a longitudinal axis thereof oriented substantially vertical. The encased soil auger apparatus is drilled into the soil until a predetermined depth is reached. The encased soil auger apparatus containing the extracted soil is then retracted and an end cap is mounted to the auger casing for enclosing the soil engaging end portion of the auger. The encased soil auger apparatus is then moved such that the longitudinal axis thereof is oriented substantially horizontal and the extracted soil contained in the auger casing is screened.

An advantage of the present disclosure is that it provides an encased soil auger apparatus for mechanical extraction and processing of soil for archeological assessments that substantially prevents "spill-in" effects.

A further advantage of the present disclosure is that it provides an encased soil auger apparatus for mechanical extraction and processing of soil for archeological assessments that enables soil extraction and soil screening using the same apparatus.

A further advantage of the present disclosure is that it provides an encased soil auger apparatus for mechanical extraction and processing of soil for archeological assessments that enables provision of water during the soil screening.

A further advantage of the present disclosure is that it provides a method of operating an encased soil auger apparatus for mechanical extraction and processing of soil for archeological assessments that enables soil extraction and soil screening using the same apparatus.

BRIEF DESCRIPTION OF THE DRAWINGS

An embodiment of the present invention is described below with reference to the accompanying drawings, in which.

DETAILED DESCRIPTION

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, certain methods and materials are now described.

While the description of certain embodiments hereinbelow is with reference to a quick mount plate for connecting the encased soil auger apparatus to the boom of a skid-steer, it will become evident to those skilled in the art that the embodiments of the invention are not limited thereto, but are adaptable for connecting the same to other light-heavy duty mechanical implements such as, for example, an excavator or tractor.

Referring to FIGS. 1a to 1e, an encased soil auger apparatus 100 according to an embodiment is provided. The encased soil auger apparatus 100 comprises an auger casing 101 forming a hollow cylindrical body. A wall of the auger casing 101 has a plurality of openings 106 disposed therein having a predetermined size for enabling passage of particles therethrough. A soil auger 102 having a helical screw blade is disposed in the auger casing 101 in a coaxial fashion—longitudinal axis 150. A soil engaging end portion 105 of the auger 102 protrudes a first end 101A of the auger casing 101. A second end 101B of the auger casing 101 is pivotally movable mounted to an auger quick mount plate 110 via split end plate and mounting ring 104, pivoting control arms 108, and auger support bracket 107, as will be described in more detail hereinbelow with reference to FIGS. 2a to 2f. The auger support bracket 107 articulates the encased soil auger apparatus 100 enabling proper vertical orientation of the same for drilling. Auger drive shaft 103 is connected to auger drive assembly 109 and pivotally movable in a conventional fashion.

Figure 1A:
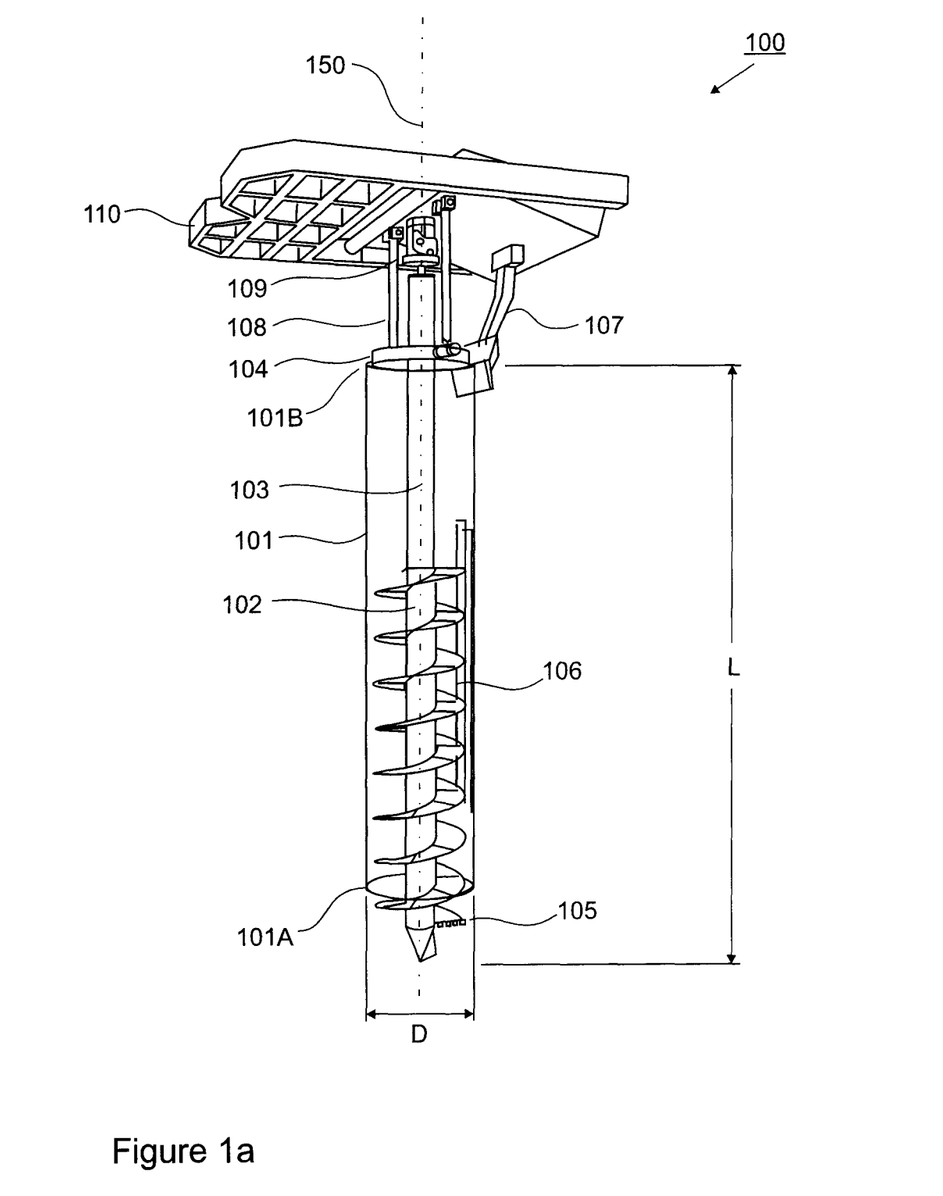
FIGS. 1a and 1b are simplified block diagrams illustrating in side perspective views an encased soil auger apparatus according to an embodiment.
Figure 1B:
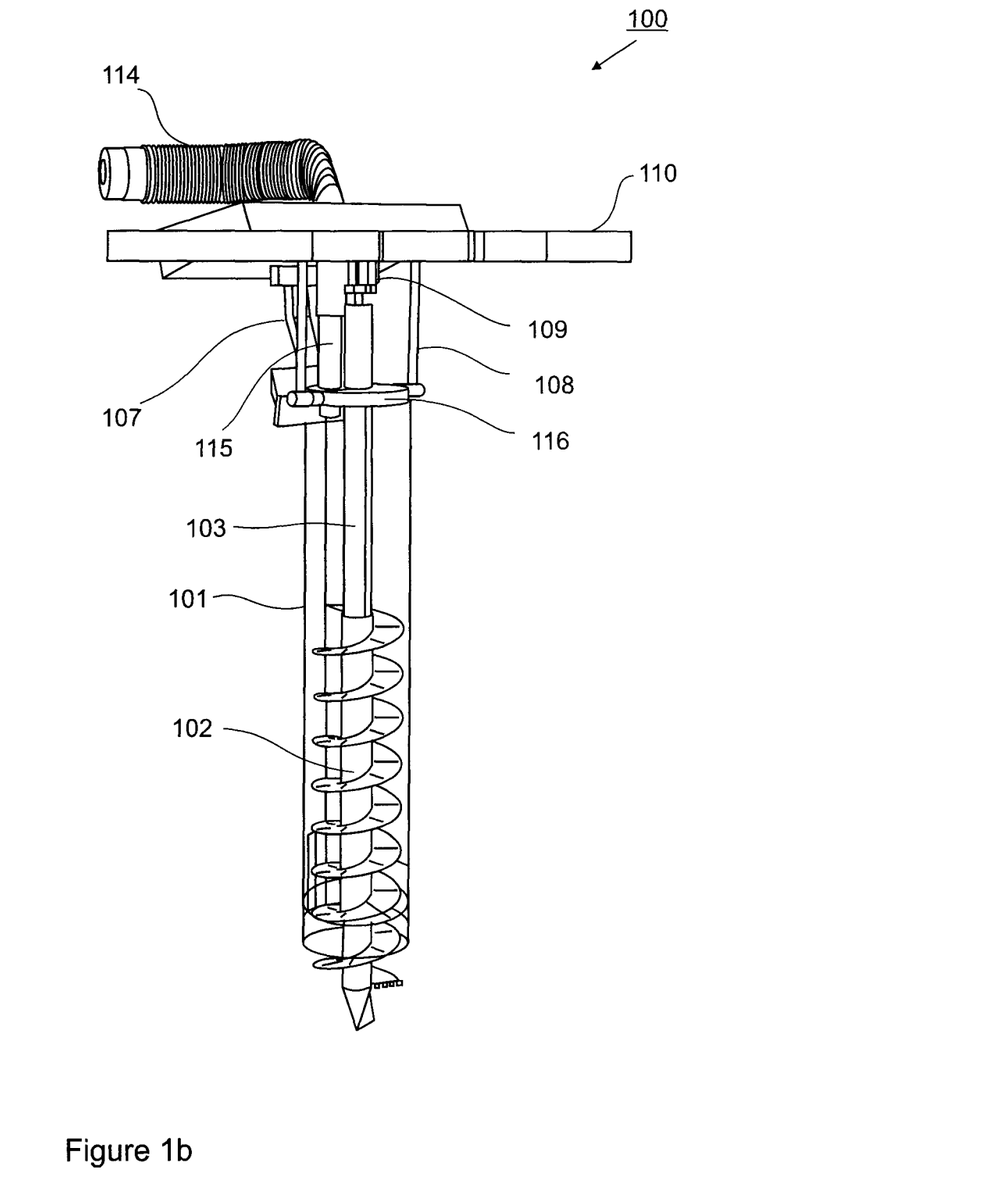

In an example implementation the encased soil auger apparatus 100 has a length L of 120 cm and a diameter D of 60 cm, enabling drilling of a standard test pit, and is driven using a hydraulic drive providing 113.5 litres per minute hydraulic pressure. Of course the encased soil auger apparatus 100 can be adapted to various different sizes, for example, having a length L greater than 120 cm, enabling testing of older sites where archaeological remains may be found at greater depths.

Optionally, as illustrated in FIG. 1b, a water inlet—in one case comprising an injector such as, for example, a spray nozzle—is disposed in end plate 116 and connected to articulating pipe 115 and flexible hose 114 via articulating pipe 115 through auger quick mount plate 110. The flexible hose 114 is, for example, connected to a water pump and water tank coupled to skid-steer 10 for pumping water for injection into the auger casing 101 during screening, as will be described hereinbelow.

Figure 1C:
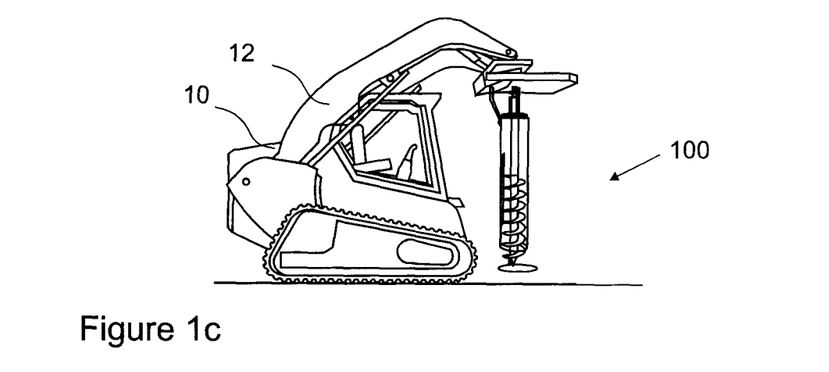
FIGS. 1c to 1e are simplified block diagrams illustrating in side perspective views the encased soil auger apparatus according to an embodiment installed on a skid steer in a raised position for drilling, fully deployed in the drilled hole, and in a horizontal position for screening soil, respectively.
Figure 1D:
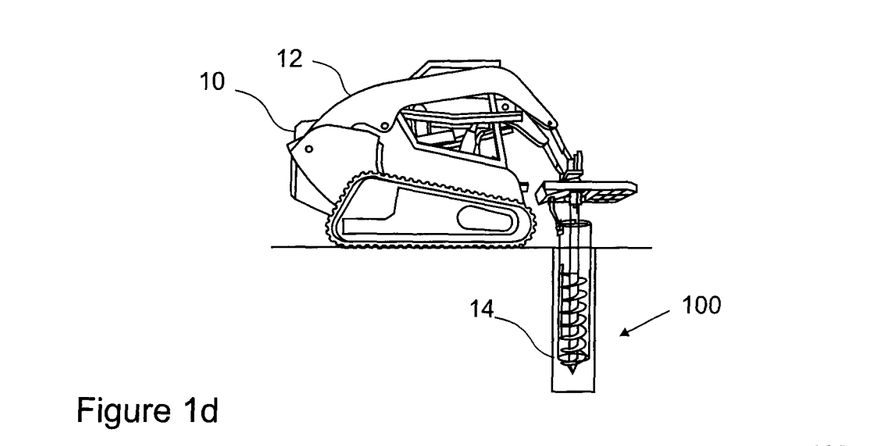
Figure 1E:
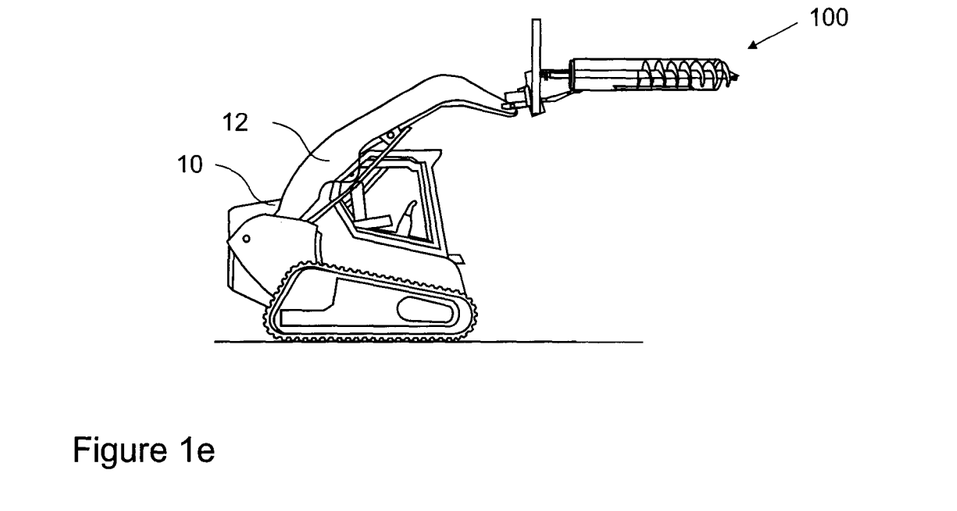
Figure 2A:
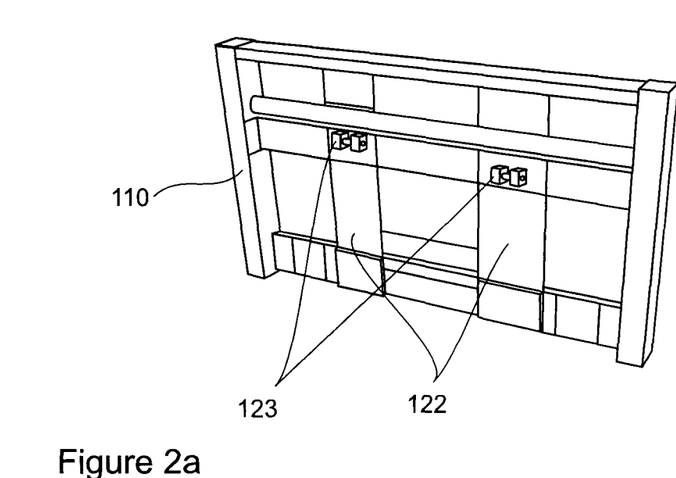
FIGS. 2a to 2c are simplified block diagrams illustrating in bottom perspective views a mounting mechanism for the encased soil auger apparatus according to an embodiment.
Figure 2B:
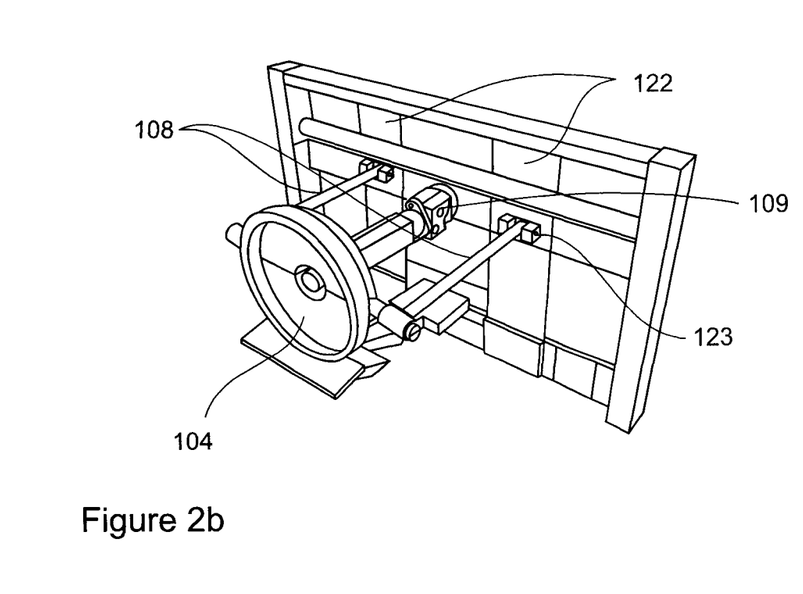
Figure 2C:
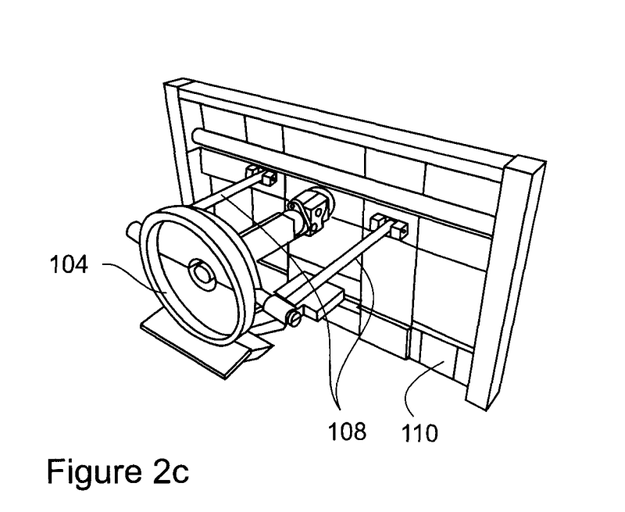
Figure 2D:
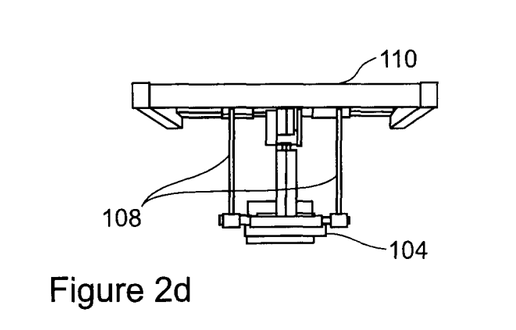
FIGS. 2d to 2f are simplified block diagrams illustrating in a front view, a side view, and a bottom view, respectively, the mounting mechanism for the encased soil auger apparatus according to an embodiment.
Figure 2E:
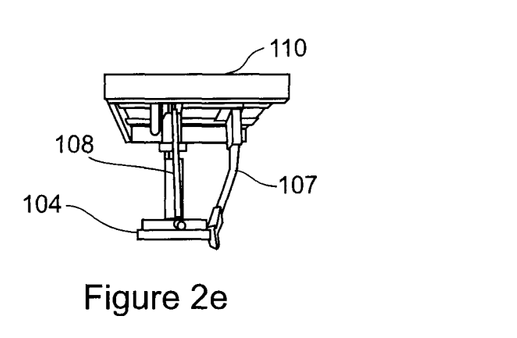
Figure 2F:
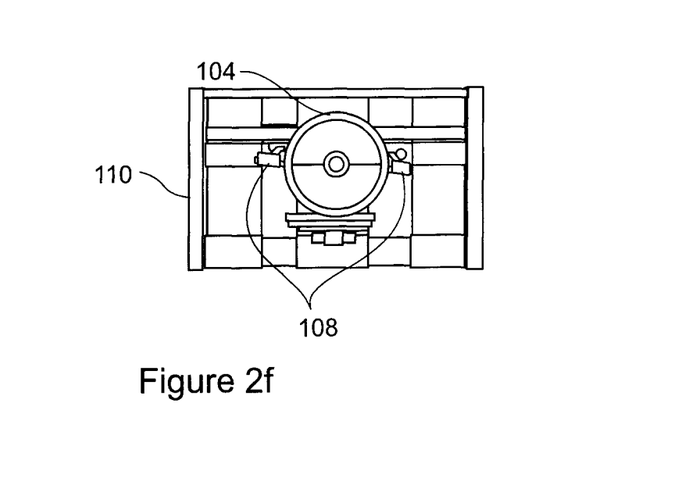

FIGS. 1c to 1e illustrate the encased soil auger apparatus 100 connected to boom 12 of the skid-steer 10 with: FIG. 1c illustrating the encased soil auger apparatus 100 in a raised vertical position prior drilling; FIG. 1d illustrating the encased soil auger apparatus 100 fully disposed in drilled test pit 14; and FIG. 1e illustrating the encased soil auger apparatus 100 a raised horizontal position for soil screening.

Referring to FIGS. 2a to 2f, the pivoting control arms 108 are, at a first end thereof, pivotally movable mounted to a commercially available auger quick mount plate 110 via, for example, steel mounting plates 122 welded to the auger quick mount plate 110 and gusseted mounting tabs 123 welded or otherwise fastened in a conventional manner to the respective steel mounting plate 122. A second end of each of the pivoting control arms 108 is pivotally movable mounted to the split end plate and mounting ring 104 in a conventional manner.

Figure 3A:
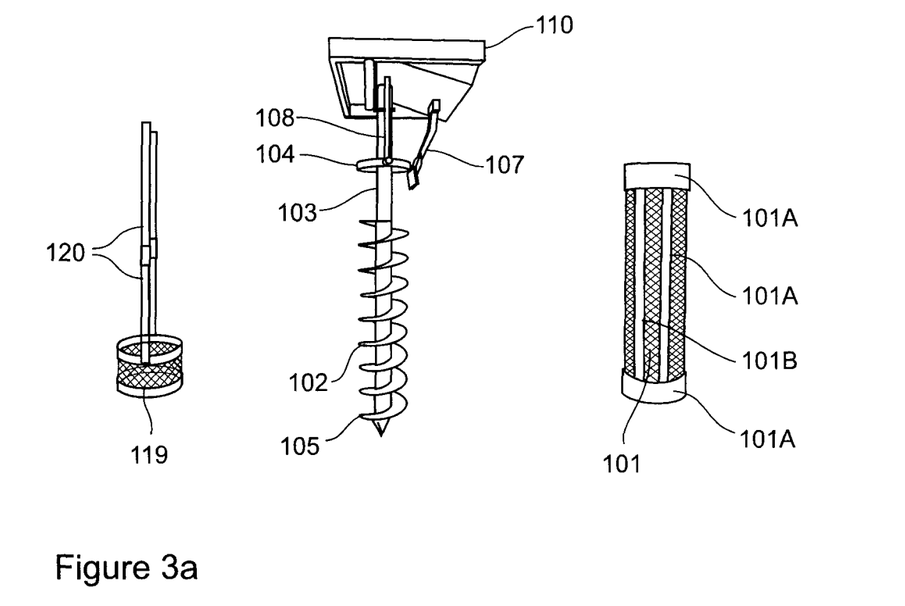
FIGS. 3a and 3b are simplified block diagrams illustrating in side perspective views the encased soil auger apparatus according to an embodiment with the auger screen and end cap separated and attached, respectively.

FIG. 3a illustrates the soil auger 102 mounted to the quick mount plate 110 with separated auger casing 101 and separated end cap 119. The auger casing 101 is made, for example, as a frame structure comprising two rings 101A forming the two end portions of the auger casing 101 and connecting members 101B with the rings 101A and connecting members 101B made of, for example, sheet material and welded together in a conventional manner. Screen 101C, for example, a steel wire mesh, is mounted to the frame structure in a conventional manner. Alternatively, the auger casing 101 is made of sheet material forming the wall thereof, for example, steel sheet material is rolled in cylindrical shape and welded in a conventional manner. Openings 106 are disposed in the sheet material in conventional manner using punching or laser cutting technology. The auger casing 101 has, in one case, a wall thickness between ⅛" and ¾" depending on the type of sediment in the test area. The mesh size or the size of the openings is determined in dependence upon the size of particles that are desired to be retained in the auger screen 101 after screening. In one case, the size is a standard size used in archaeological testing, for example ¼". Optionally, auger casings 101 having different screen sizes, for example, ⅛", are provided, in order to enable changing of the screen size during testing, for example, depending if archaeological remains have been found or not. The second end of the auger casing 101 is mounted to the mounting ring 104 in a conventional manner using, for example, screw fasteners or a clamping mechanism, enabling simple mounting/removal of the same.

End cap 119 is made in a similar fashion as the auger casing 101 as a frame structure with a wire mesh or made of sheet material having openings disposed therein. Optionally, the openings re omitted in the end cap 119. The end cap 119 further comprises a fastening mechanism such as, for example, chain binders or ratchet straps 120 to easily and removably attach the same to the auger casing 101. The end cap 119 is employed for enclosing the soil engaging end portion of the auger after extraction of the soil and during screening.

Figure 3B:
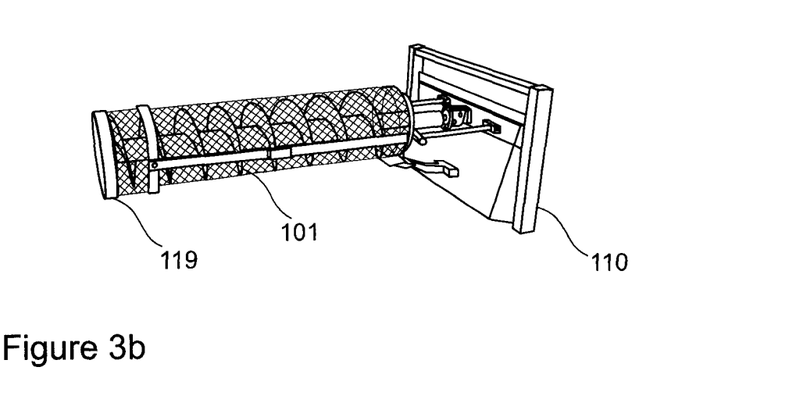

FIG. 3b illustrates the soil auger 102 having the auger casing 101 and the end cap 119 mounted thereto, as it is used after extraction of the soil and during screening.

Figures 4A, 4B:
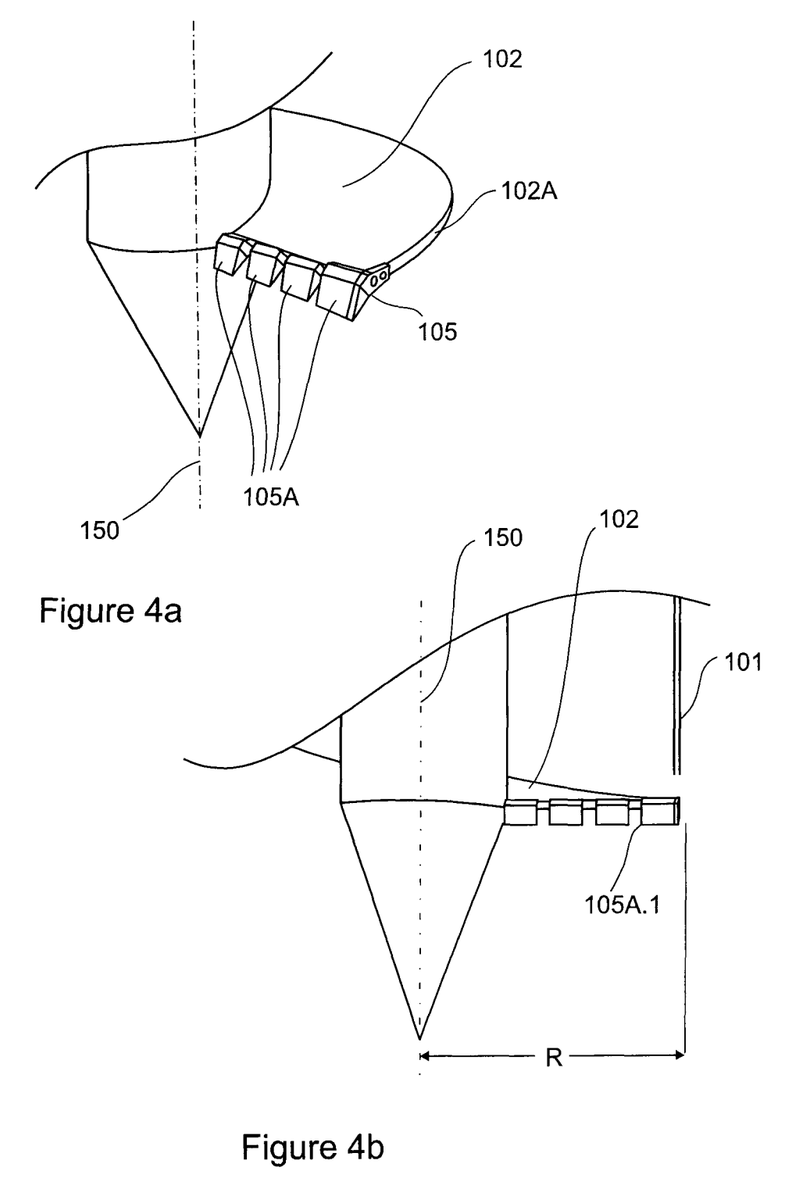
FIGS. 4a and 4b are simplified block diagrams illustrating in a side perspective view and a side view a soil engaging end portion of the auger screw blade of the encased soil auger apparatus according to an embodiment; and, FIGS. 5a to 5h are simplified block diagrams illustrating in side perspective views the encased soil auger apparatus according to an embodiment installed on a skid steer in different modes of operation.

As illustrated in FIGS. 4a and 4b, the soil engaging end portion 105 of the auger 102 extends from the longitudinal axis 150 approximately a same distance as an outside radius R of the auger casing 101, in order to provide clearance for the auger casing in the borehole. In one case, the soil engaging end portion 105 comprises a plurality of cutting teeth 105A with an outer cutting tooth 105A.1 extending from an outside edge 102A of the auger screw blade 102.

Figure 5A:
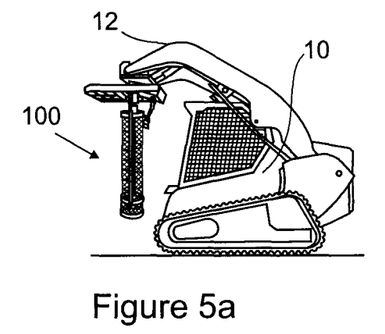
Figure 5B:
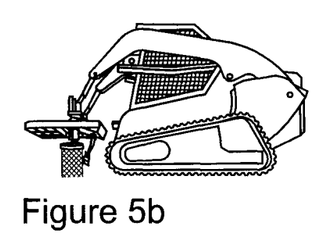
Figure 5C:
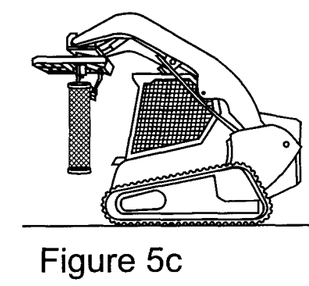
Figure 5D:
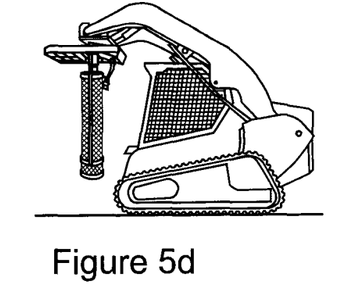
Figure 5E:
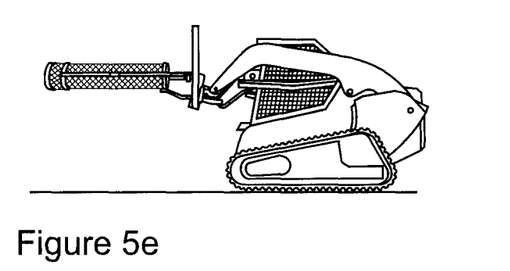
Figure 5F:
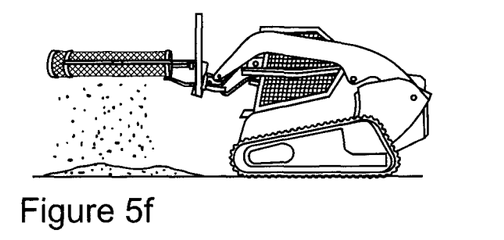
Figure 5G:
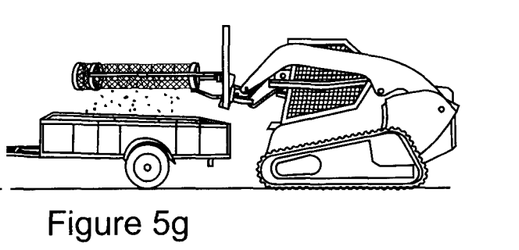
Figure 5H:
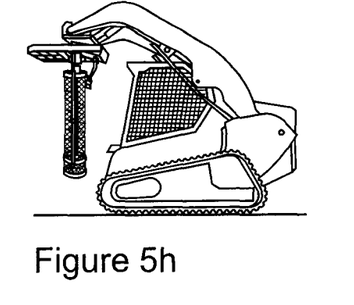

Referring to FIGS. 5a to 5h, a method of extracting and processing soil according to an embodiment of the invention is provided. In an example implementation the encased soil auger apparatus 100 is mounted to the boom 12 of the skid-steer 10. The encased soil auger apparatus 100 is placed at a predetermined location with the longitudinal axis thereof oriented substantially vertical, as illustrated in FIG. 5a. When in place, the encased soil auger apparatus 100 is drilled into the soil until a predetermined depth, for example, 120 cm, is reached, as illustrated in FIG. 5b. The encased soil auger apparatus 100 containing the extracted soil is then retracted and, after the complete removal of the encased soil auger apparatus 100 from the borehole, end cap 119 is mounted to the auger casing 101 to enclose the soil engaging end portion of the soil auger 102, as illustrated in FIGS. 5c and 5d, respectively. The end cap 119 can be mounted to the auger casing 101 immediately after complete removal of the encased soil auger apparatus 100 from the borehole in order to prevent spillage of the extracted soil. The encased soil auger apparatus 100 is then moved such that the longitudinal axis thereof is oriented substantially horizontal, as illustrated in FIG. 5e. The extracted soil contained in the auger casing 101 is then screened, for example, by rotating the soil auger 102 clockwise and counterclockwise in an alternating fashion. Smaller particles of the screened soil fall to the ground or are collected in a respective receptacle, as illustrated in FIGS. 5f and 5g, respectively. After screening, larger objects are collected in the end cap 119, for example, by moving the encased soil auger apparatus such that the longitudinal axis thereof is oriented substantially vertical and rotating the soil auger to transport the remaining larger objects into the end cap 119. The end cap 119 with the collected larger objects is then removed from the auger casing 101 and the encased soil auger apparatus 100 is ready for drilling the next test pit, as illustrated in FIG. 5h. The collected larger objects are then investigated by an archaeologist to determine if the test pit is positive or negative for archaeological remains. Optionally, water is injected into the auger casing 101 during screening, FIGS. 5f and 5g.

The present invention has been described herein with regard to certain embodiments. However, it will be obvious to persons skilled in the art that a number of variations and modifications can be made without departing from the scope of the invention as described herein.

What is claimed is:

1. An encased soil auger apparatus for extracting and screening soil comprising:
   an auger casing forming a hollow cylindrical body, the auger casing comprising a screen for screening the soil such that particles larger than a predetermined size are retained inside the auger casing;
   and, a soil auger having a helical screw blade disposed in the auger casing in a coaxial fashion, a soil engaging end portion of the auger protruding from a first end of the auger casing.

2. The encased soil auger apparatus according to claim 1 wherein the soil engaging end portion of the auger extends from a longitudinal axis approximately a same distance as an outside radius of the auger casing.

3. The encased soil auger apparatus according to claim 2 wherein the soil engaging end portion of the auger comprises a plurality of cutting teeth with an outer cutting tooth extending from an outside edge of the auger screw blade.

4. The encased soil auger apparatus according to claim 1 comprising an end plate mounted to a second end of the auger casing.

5. The encased soil auger apparatus according to claim 1 comprising an end cap for enclosing the soil engaging end portion of the auger after extraction of the soil.

6. The encased soil auger apparatus according to claim 5 wherein a wall of the end cap has a plurality of openings having a predetermined size for enabling passage of particles therethrough.

7. The encased soil auger apparatus according to claim 1 comprising a water inlet for injecting water into the auger casing, the water inlet being placed in proximity to a second end of the auger casing.

8. A method of extracting and screening soil comprising:
   providing an encased soil auger apparatus comprising:
      an auger casing forming a hollow cylindrical body, a wall of the auger casing having a plurality of openings having a predetermined size for enabling passage of particles therethrough; and,
      a soil auger having a helical screw blade disposed in the auger casing in a coaxial fashion, a soil engaging end portion of the auger protruding from a first end of the auger casing;
   placing the encased soil auger apparatus at a predetermined location with a longitudinal axis thereof oriented substantially vertical;

drilling the encased soil auger apparatus into the soil until a predetermined depth is reached;

retracting the encased soil auger apparatus containing the extracted soil;

using an end cap enclosing the soil engaging end portion of the auger;

moving the encased soil auger apparatus such that the longitudinal axis thereof is oriented substantially horizontal; and, screening the extracted soil.

9. The method according to claim 8 wherein during screening the soil auger is rotated clockwise and counter-clockwise in an alternating fashion.

10. The method according to claim 8 comprising collecting larger objects in the end cap by moving the encased soil auger apparatus such that the longitudinal axis thereof is oriented substantially vertical.

11. The method according to claim 8 comprising injecting water into the auger casing during screening.

* * * * *